(12) United States Patent
Zhang et al.

(10) Patent No.: US 7,587,240 B2
(45) Date of Patent: Sep. 8, 2009

(54) ATRIAL CAPTURE VERIFICATION

(75) Inventors: Geng Zhang, Newbury Park, CA (US); Ankur Garg, Minneapolis, MN (US); Douglas R. Daum, Oakdale, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 206 days.

(21) Appl. No.: 11/012,433

(22) Filed: Dec. 15, 2004

(65) Prior Publication Data

US 2006/0129197 A1 Jun. 15, 2006

(51) Int. Cl.
*A61N 1/365* (2006.01)
(52) U.S. Cl. ................ 607/14; 607/9; 607/27; 607/28
(58) Field of Classification Search .............. 607/9, 607/14, 27–28
See application file for complete search history.

(56) References Cited

U.S. PATENT DOCUMENTS

| | | | |
|---|---|---|---|
| 4,505,276 A | 3/1985 | Markowitz et al. | |
| 4,543,963 A | 10/1985 | Gessman | |
| 4,569,350 A | 2/1986 | Mumford et al. | |
| 5,000,189 A | 3/1991 | Throne et al. | |
| 5,217,021 A | 6/1993 | Steinhaus et al. | |
| 5,253,644 A | 10/1993 | Elmvist | |
| 5,273,035 A | 12/1993 | Markowitz et al. | |
| 5,312,450 A | 5/1994 | Markowitz | |
| 5,350,410 A | 9/1994 | Kleks et al. | |
| 5,374,280 A | 12/1994 | Den Dulk | |
| 5,383,910 A | 1/1995 | Den Dulk | |
| 5,447,519 A | 9/1995 | Peterson | |
| 5,458,623 A | 10/1995 | Lu et al. | |
| 5,476,482 A | 12/1995 | Lu | |
| 5,534,017 A | 7/1996 | Van Krieken et al. | |
| 5,549,648 A | 8/1996 | Stoop | |
| 5,601,615 A * | 2/1997 | Markowitz et al. | 607/28 |
| 5,653,738 A | 8/1997 | Sholder | |
| 5,683,431 A | 11/1997 | Wang | |
| 5,713,933 A | 2/1998 | Greeninger et al. | |
| 5,766,229 A | 6/1998 | Bornzin | |
| 5,779,645 A | 7/1998 | Olson et al. | |
| 5,817,027 A | 10/1998 | Arand et al. | |
| 5,843,137 A | 12/1998 | Condie et al. | |
| 5,857,977 A | 1/1999 | Caswell et al. | |
| 5,871,509 A | 2/1999 | Noren | |
| 6,038,474 A | 3/2000 | Zhu et al. | |
| 6,052,620 A | 4/2000 | Gillberg et al. | |
| 6,076,014 A | 6/2000 | Alt | |
| 6,101,416 A | 8/2000 | Sloman | |

(Continued)

FOREIGN PATENT DOCUMENTS

EP 1116494 7/2001

*Primary Examiner*—Carl H Layno
*Assistant Examiner*—Deborah Malamud
(74) *Attorney, Agent, or Firm*—Hollingsworth & Funk, LLC

(57) ABSTRACT

Methods and systems for classifying cardiac responses to pacing stimulation and/or preventing retrograde cardiac conduction are described. Following delivery of a pacing pulse to an atrium of the patient'heart during a cardiac cycle, the system senses in the atrium for a retrograde P-wave. The system classifies the atrial response to the pacing pulse based on detection of the retrograde P-wave. The system may also sense for an atrial evoked response and utilize the atrial evoked response in classifying the cardiac pacing response.

19 Claims, 12 Drawing Sheets

U.S. PATENT DOCUMENTS

| | | |
|---|---|---|
| 6,128,535 A | 10/2000 | Maarse |
| 6,163,724 A | 12/2000 | Hemming et al. |
| 6,167,307 A | 12/2000 | Hess |
| 6,175,766 B1 | 1/2001 | Bornzin et al. |
| 6,221,011 B1 | 4/2001 | Bardy |
| 6,259,950 B1 | 7/2001 | Mann et al. |
| 6,270,457 B1 | 8/2001 | Bardy |
| 6,275,731 B1 | 8/2001 | Zhu et al. |
| 6,277,072 B1 | 8/2001 | Bardy |
| 6,280,380 B1 | 8/2001 | Bardy |
| 6,312,378 B1 | 11/2001 | Bardy |
| 6,336,903 B1 | 1/2002 | Bardy |
| 6,358,203 B2 | 3/2002 | Bardy |
| 6,363,281 B1 | 3/2002 | Zhu et al. |
| 6,368,284 B1 | 4/2002 | Bardy |
| 6,389,316 B1 | 5/2002 | Bornzin et al. |
| 6,398,728 B1 | 6/2002 | Bardy |
| 6,408,210 B1 | 6/2002 | Bornzin et al. |
| 6,418,343 B1 | 7/2002 | Zhang et al. |
| 6,440,066 B1 | 8/2002 | Bardy |
| 6,449,503 B1 | 9/2002 | Hsu |
| 6,456,881 B1 | 9/2002 | Bornzin et al. |
| 6,473,649 B1 | 10/2002 | Gryzwa et al. |
| 6,496,730 B1 | 12/2002 | Kleckner et al. |
| 6,498,949 B2 | 12/2002 | Levine et al. |
| 6,505,070 B1 | 1/2003 | Backers |
| 6,505,071 B1 | 1/2003 | Zhu et al. |
| 6,609,028 B2 | 8/2003 | Struble |
| 6,611,714 B1 | 8/2003 | Mo |
| 6,625,489 B2 | 9/2003 | Sheth et al. |
| 6,684,100 B1 | 1/2004 | Sweeney et al. |
| 6,697,673 B1 | 2/2004 | Lu |
| 6,721,601 B1 | 4/2004 | Bornzin et al. |
| 6,925,326 B1 | 8/2005 | Levine et al. |
| 6,950,704 B1 | 9/2005 | Bradley |
| 7,072,714 B2 | 7/2006 | Busch et al. |
| 7,076,297 B2 | 7/2006 | Limousin et al. |
| 7,123,954 B2 | 10/2006 | Narayan et al. |
| 7,130,685 B2 | 10/2006 | Casavant et al. |
| 7,130,690 B2 | 10/2006 | Rueter et al. |
| 7,177,685 B2 | 2/2007 | Lincoln et al. |
| 2002/0120303 A1 | 8/2002 | Levine et al. |
| 2003/0125777 A1 | 7/2003 | Ding et al. |
| 2004/0260348 A1 | 12/2004 | Bakken et al. |
| 2005/0080347 A1 | 4/2005 | Sheth et al. |
| 2005/0131476 A1 | 6/2005 | Kim et al. |
| 2005/0131477 A1 | 6/2005 | Meyer et al. |

* cited by examiner

ATRIAL CAPTURE VERIFICATION

RELATED PATENT DOCUMENT

This patent application is related to commonly owned U.S. Patent Application identified by, now U.S. Publication No. 2006/0129199, entitled "Atrial Retrograde Management," filed concurrently herewith and incorporated herein by reference.

FIELD OF THE INVENTION

The present invention relates generally to implantable medical devices and, more particularly, to verifying atrial capture following delivery of a pacing pulse.

BACKGROUND OF THE INVENTION

When functioning normally, the heart produces rhythmic contractions and is capable of efficiently pumping blood throughout the body. However, due to disease or injury, the heart rhythm may become irregular resulting in diminished pumping efficiency.

Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically include circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal following the contraction is denoted the captured response (CR). The captured response may include an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold may be required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Capture detection allows the cardiac rhythm management system to adjust the energy level of pace pulses to correspond to the optimum energy expenditure that reliably produces a contraction. Further, capture detection allows the cardiac rhythm management system to initiate a back-up pulse at a higher energy level whenever a pace pulse does not produce a contraction.

Retrograde conduction may occur, for example, when a depolarization wave initiated in a ventricle by a pacing pulse or intrinsic activation travels back to the atrium producing a retrograde P-wave. Retrograde P-waves may inhibit effective atrial pacing. A pacing pulse delivered to the atrium will not result in capture if the atrial tissue is refractory due to a retrograde P-wave. Further, retrograde conduction to the atrium may cause pacemaker mediated tachycardia.

There is a need in the technology for methods and systems that reliably determine if a pacing pulse captures an atrium. There is a further need for methods and systems that provide atrial retrograde management. The present invention fulfills these and other needs.

SUMMARY OF THE INVENTION

The present invention is directed to methods and systems for classifying cardiac responses to atrial pacing. One embodiment of the invention involves a method for classifying a cardiac response to pacing. A pacing pulse is delivered to an atrium during a cardiac cycle. A pacing pulse is delivered to an atrium if an intrinsic ventricular activation is not sensed during the cardiac cycle. If, responsive to the ventricular pacing pulse or the intrinsic ventricular activation, a retrograde P-wave is detected in the atrium, the cardiac response to the atrial pacing pulse is classified as a non-captured response.

According to one aspect of the invention, if an atrial evoked response is not detected and a retrograde P-wave responsive to the ventricular pacing pulse or intrinsic activation is detected, the cardiac response to the atrial pacing pulse is classified as a non-captured response.

In yet another embodiment of the invention, a cardiac system includes a plurality of implantable electrodes configured for one or more of sensing a cardiac signal and delivering cardiac pacing pulses to a patient. A housing is configured for implantation in the patient. A controller is provided in the housing and is coupled to the plurality of implantable electrodes. The controller is configured to deliver a pacing pulse to an atrium of the patient's heart during a cardiac cycle, sense for an intrinsic activation of a ventricle during the cardiac cycle, deliver a pacing pulse to the ventricle if the intrinsic activation is not sensed during the cardiac cycle. The cardiac system senses in the atrium for a retrograde P-wave in response to the ventricular pacing pulse or the intrinsic activation. The cardiac response is classified as a non-captured response if the retrograde P-wave is detected.

The above summary of the present invention is not intended to describe each embodiment or every implementation of the present invention. Advantages and attainments, together with a more complete understanding of the inven-

Figure 1A:
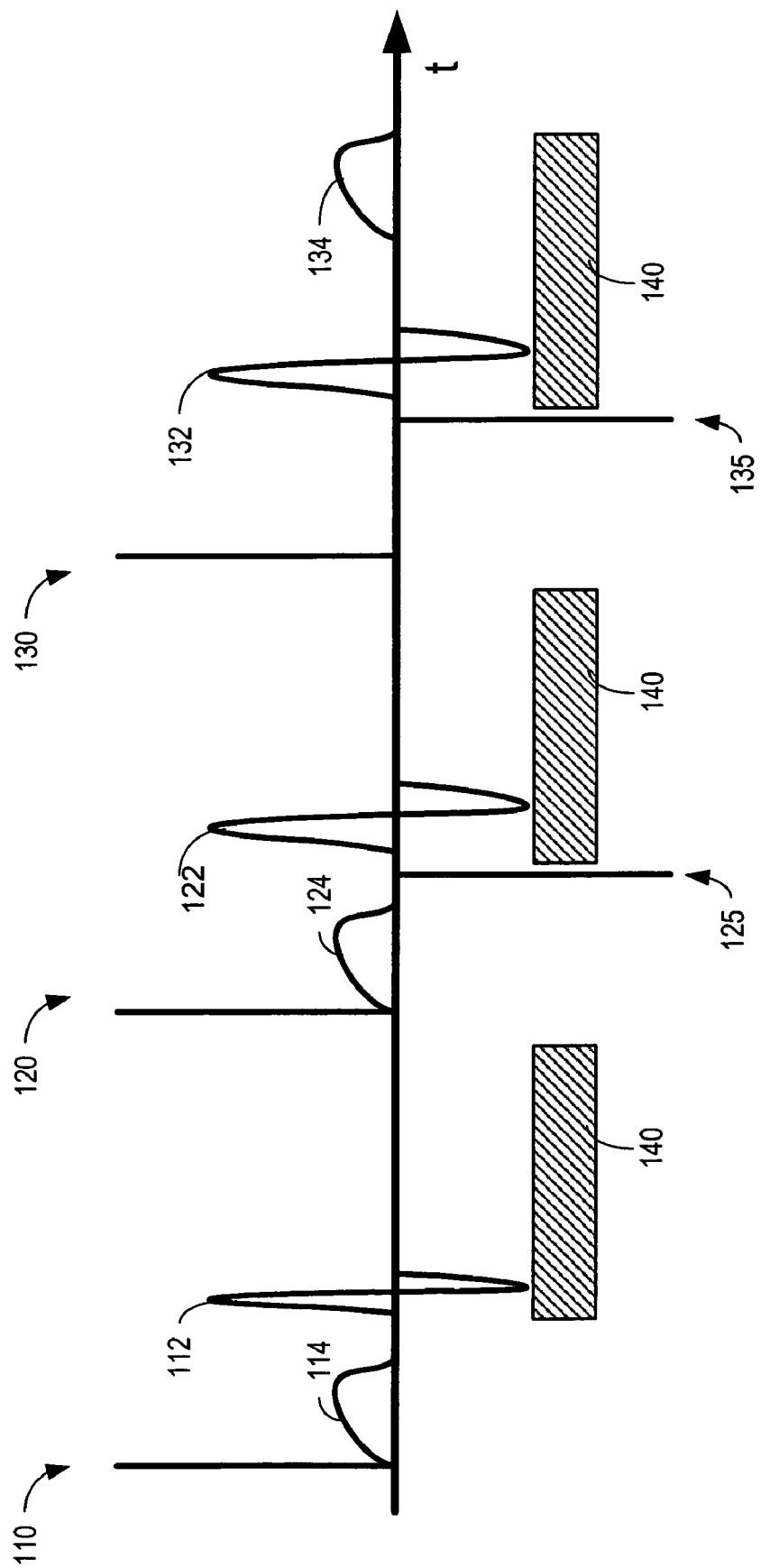
FIG. 1A is a graph illustrating a method of confirming atrial loss of capture in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown, by way of illustration, various embodiments by which the invention may be practiced. It is to be understood that other embodiments may be utilized, and structural and functional changes may be made without departing from the scope of the present invention.

After delivery of a pacing pulse to a heart chamber, various cardiac responses to the pacing pulse are possible. In one scenario, the pacing pulse may generate a propagating wavefront of depolarization resulting in a contraction of the heart chamber. In this scenario, the pacing pulse is said to have captured the heart chamber. Capture of the heart chamber may occur if the pacing pulse has sufficient energy and is delivered during a non-refractory period. If the pacing pulse does not produce contraction of the chamber, the cardiac response is referred to as non-capture or loss of capture. Non-capture may occur, for example, if the pacing pulse energy is too low, and/or if the pacing pulse is delivered during a refractory period of the cardiac tissue.

By way of example, the processes of the present invention may be used in capture threshold testing to determine the optimal energy for pacing. The minimum pacing energy that produces capture is referred to as the capture threshold. It is desirable for a pace pulse to have sufficient energy to capture the heart without expending excess energy above the capture threshold. Thus, accurate determination of the capture threshold may be desirable for efficient pacing.

Those skilled in the art will appreciate that reference to a capture threshold testing procedure indicates a method of determining the capture threshold in one or more of the left atrium, right atrium, left ventricle, and right ventricle. In such a procedure, the pacemaker, automatically or upon command, initiates a search for the capture threshold of the selected heart chamber. The capture threshold is defined as the lowest pacing energy that consistently captures the heart.

In one example of an automatic capture threshold procedure, the pacemaker delivers a sequence of pacing pulses to the heart and detects the cardiac responses to the pace pulses. The energy of the pacing pulses may be decreased in discrete steps until a predetermined number of loss-of-capture responses occur. The pacemaker may increase the stimulation energy in discrete steps until a predetermined number of capture responses occur to confirm the capture threshold. A capture threshold test may be performed using cardiac response classification methods of the present invention.

Other procedures for implementing capture threshold testing may be utilized. In one example, the pacing energy may be increased in discrete steps until capture is detected. In another example, the pacing energy may be adjusted according to a binomial search pattern.

Capture threshold determination is distinguishable from automatic capture detection, a procedure that typically occurs on a beat-by-beat basis during pacing. Automatic capture detection verifies that a delivered pace pulse results in a captured response. When a captured response is not detected following a pace pulse, the pacemaker may deliver a back up safety pace to ensure consistent pacing. The back up pace may be delivered, for example, about 70-80 ms after the initial pace pulse. If a predetermined number of pace pulses delivered during normal pacing do not produce a captured response, the pacemaker may initiate a capture threshold test to determine the capture threshold. Alternatively, if a predetermined number of pacing pulses do not produce a captured response, the pacemaker may adjust the pacing energy for the next pacing pulse. Atrial capture verification and atrial retrograde management may be implemented using processes of the present invention.

Embodiments of the invention are directed to methods and systems for determining if an atrial pacing pulse captures or fails to capture the atrium. Loss of capture determination may be based on detection of a ventricular depolarization wave that travels back to the atrium—retrograde conduction. This retrograde depolarization wave may be sensed and used in capture verification processes of the present invention.

When a ventricular depolarization occurs, either intrinsically, or as a result of a ventricular pace, the depolarization wavefront may travel towards the atrium if the atrial tissue is not in its refractory period. If the myocardial tissue of the atrium is not refractory (i.e., if there was no intrinsic P-wave or the atrium was not captured by an atrial pacing pulse preceding the ventricular depolarization), then the wavefront initiated by the ventricular depolarization is more likely to be retrogradely conducted and sensed in the atrium as a retrograde P-wave. Thus, sensing a retrograde P-wave indicates that the atrial pacing pulse did not capture the atrium.

Further embodiments of the invention involve approaches for avoiding or managing atrial retrograde conduction when an atrial pacing pulse does not capture the atrium. According to some embodiments, a back up pace can be delivered to the atrium following loss of capture event. Backup pacing is delivered at a relatively high energy level to ensure capture and thus prevents retrograde conduction to the atrium.

Other retrograde management approaches described herein involve delaying the next scheduled pace if a retrograde P-wave is detected. Following detection of the retrograde P-wave, the next scheduled atrial pace is delayed until expiration of an effective atrial refractory period. Delaying the next scheduled pace allows the myocardium to recover from its refractory due to the retrograde conduction before the next pacing pulse is delivered.

FIG. 1A is a graph illustrating a method of confirming atrial loss of capture in accordance with embodiments of the invention. This method may be used, for example, in a dual chamber device. When atrial capture is lost, AV synchrony may be disrupted, and a ventricular pulse may occur after the failed atrial pulse when an atrioventricular delay expires. Because the ventricle is activated before the atrium, the excitation may travel up to activate the atrium as retrograde conduction.

In the graph of FIG. 1A, an atrial pacing pulse 110 that captures the atrium is followed by an evoked atrial response (AER) 114, and an intrinsic ventricular response 112, which is a QRS complex. A post ventricular atrial refractory period (PVARP) 140 is illustrated following the intrinsic ventricular response 112. This is an atrial paced heartbeat with intrinsic ventricular response.

The next heartbeat begins with an atrial pacing pulse 120 that captured the atrium. The atrial pacing pulse 120 is followed by an atrial evoked response 124. A ventricular pacing pulse 125 is delivered which captures the ventricle producing a ventricular evoked response 122. The ventricular evoked response shows a widened QRS complex relative to the intrinsic ventricular response 112. A PVARP 140 is illustrated following the ventricular pacing pulse 125.

The final heartbeat of FIG. 1A illustrates an atrial retrograde conduction. The atrial pacing pulse 130 does not capture the atrium, thus an atrial evoked response is not sensed. The atrial pacing pulse 130 is followed, after an atrioventricular delay, by a ventricular pacing pulse 135, and a ventricular evoked response 132, showing a widened QRS complex relative to the intrinsic ventricular response 112. A PVARP 140 is illustrated following the ventricular pulse 135. An atrial P-wave 134 is illustrated within the PVARP 140 following the ventricular pulse 135. The retrograde P-wave is produced by a depolarization wavefront initiated by the ventricular pulse 135 and conducted to the atrium. If retrograde conduction occurs in close proximity to a scheduled atrial pacing pulse, capture of the atrium may not occur regardless of the pulse being greater than a capture threshold.

Figure 1B:
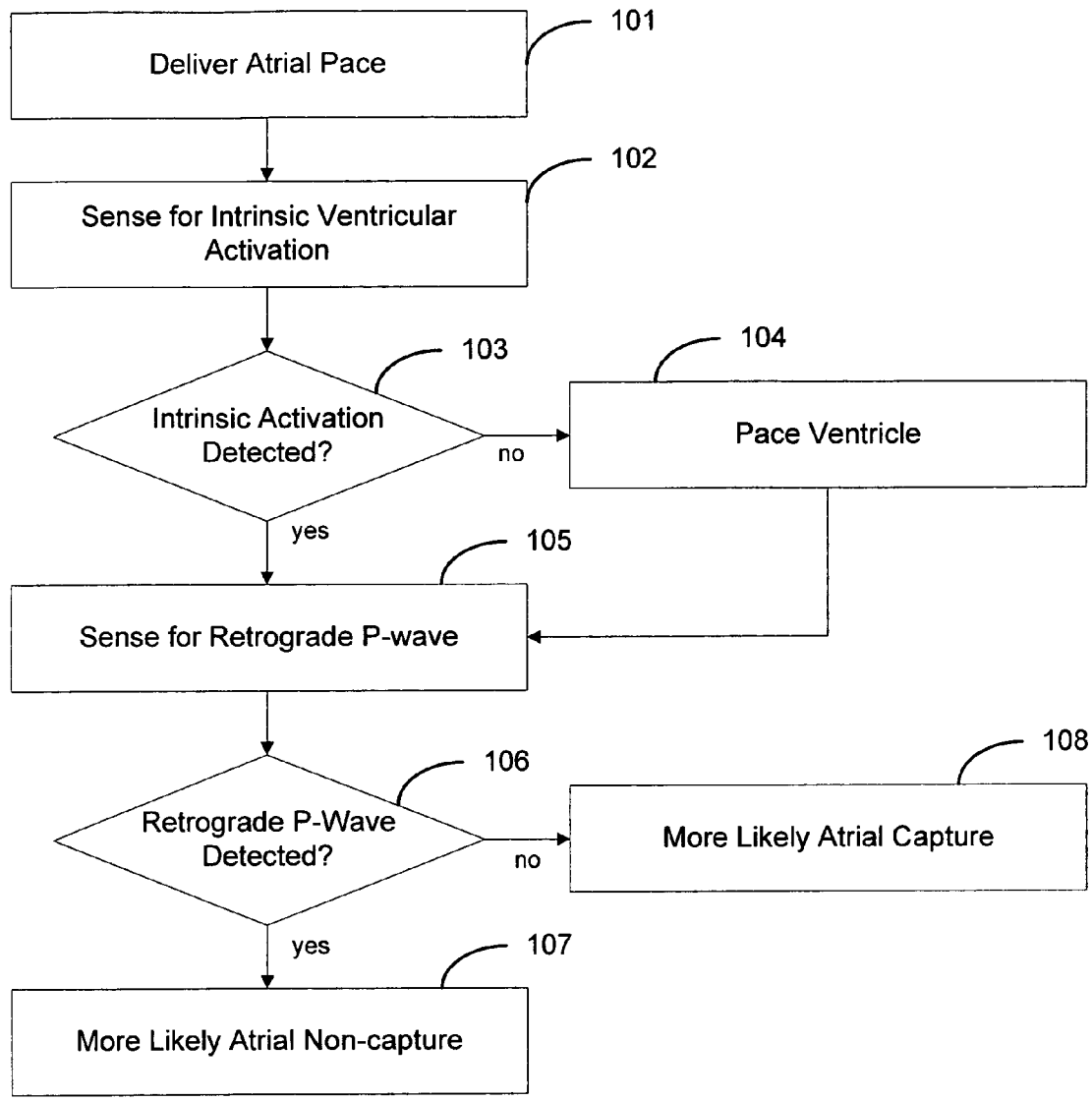
FIG. 1B is a flowchart illustrating a method of atrial capture verification in accordance with embodiments of the invention.
Figure 1C:
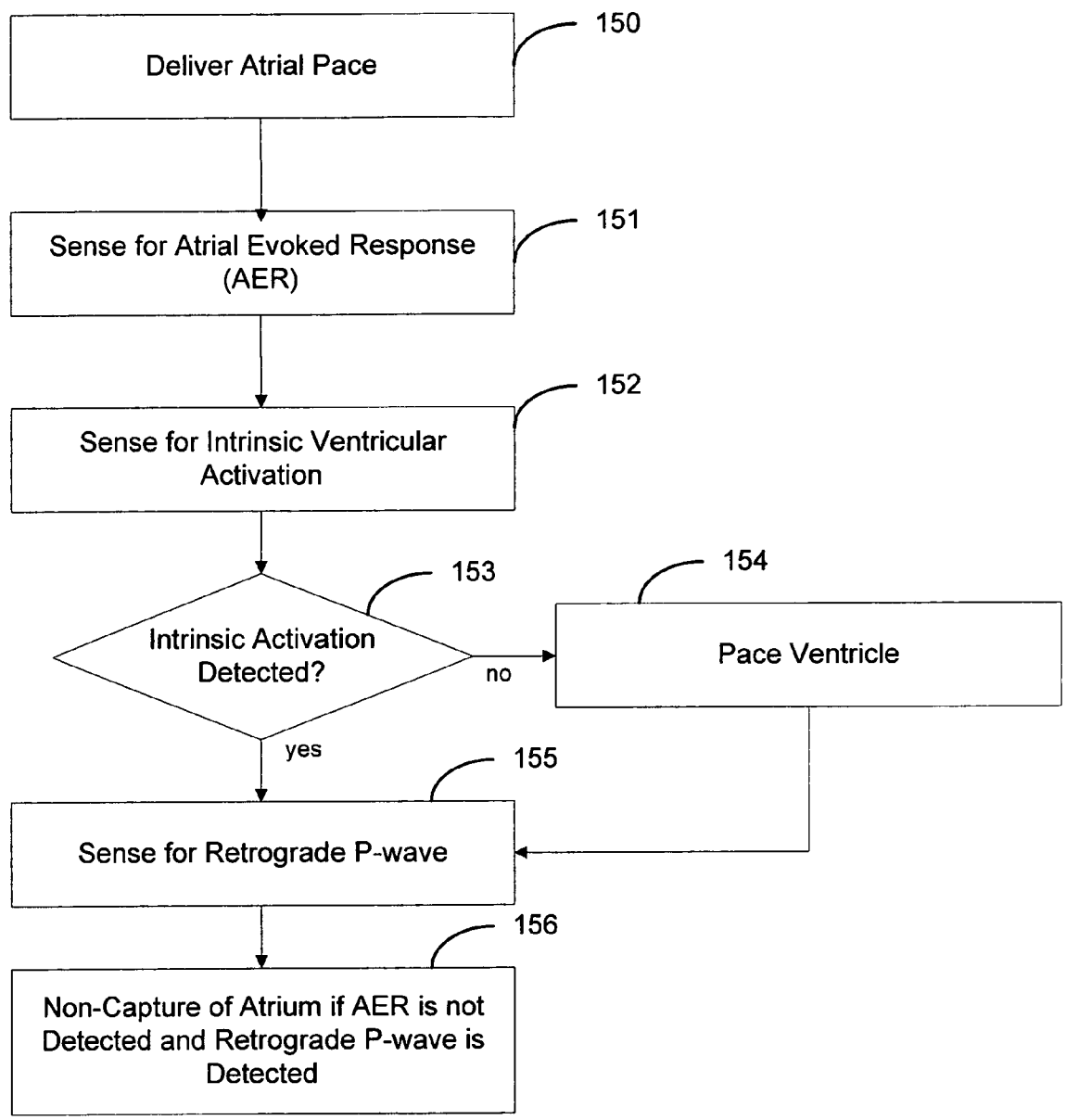
FIG. 1C is a flowchart illustrating a method of determining a cardiac response to a pacing pulse using both an atrial evoked response and retrograde P-wave detection in accordance with embodiments of the invention

The atrial evoked response and/or retrograde P-wave occurring during a cardiac cycle may be utilized both for atrial capture verification and/or atrial retrograde management. FIGS. 1B-1C are flowcharts illustrating atrial capture verification in accordance with embodiments of the invention. The flowchart of FIG. 1B illustrates capture verification based on a sensed retrograde P-wave. A pacing pulse is delivered 101 to an atrium during a cardiac cycle. The system senses for 102 an intrinsic activation of a ventricle during the cardiac cycle. If intrinsic ventricular activation is not sensed 103, then a pacing pulse is delivered 104 to the ventricle.

The system senses for 105 a retrograde P-wave responsive to the intrinsic ventricular activation or the ventricular pace. If the retrograde P-wave is detected 106, then atrial non-capture is more likely 107. If the retrograde P-wave is not detected 106, then the system may classify 109 the cardiac response to the atrial pace as a captured response.

The flowchart of FIG. 1C illustrates a method of determining a cardiac response to a pacing pulse using both an atrial evoked response and retrograde P-wave detection. Use of both the atrial evoked response and retrograde P-wave detection enhances the accuracy of capture verification processes. An atrial pacing pulse is delivered 150. The system senses for 151 an atrial evoked response following the atrial pacing. The system senses for 152 an intrinsic ventricular depolarization. A pacing pulse is delivered 154 to the ventricle if an intrinsic activation of the ventricle is not detected 153.

Following delivery of the ventricular pace or the intrinsic ventricular depolarization, the system senses in the atrium for 155 a retrograde P-wave. The cardiac response to the atrial pacing pulse is classified 156 as a non-captured response if the retrograde P-wave is detected and the atrial evoked response is not detected.

Figure 1D:
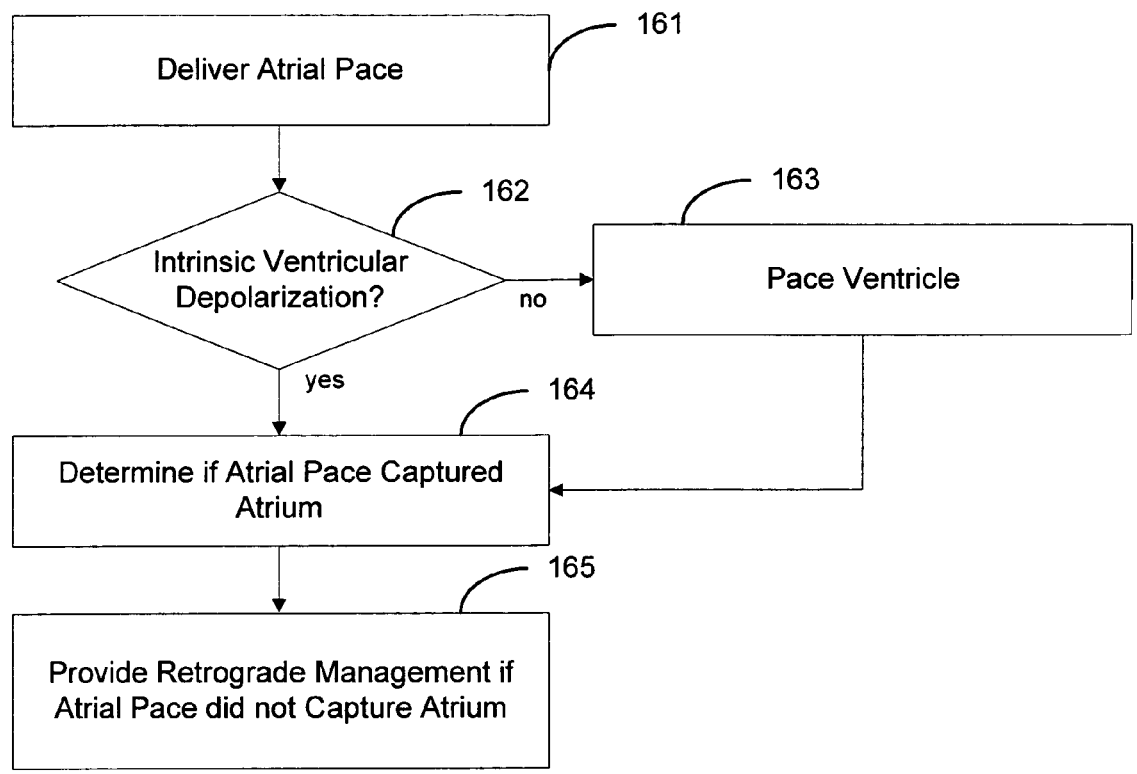
FIG. 1D is a flowchart illustrating a method of retrograde management in accordance with embodiments of the invention.

As previously discussed non-capture of the atrium may result in a series of retrograde P-waves which are undesirable for effective pacing. Various embodiments involve the providing retrograde management if atrial non-capture is detected. The flowchart of FIG. 1D illustrates a method of retrograde management in accordance with embodiments of the invention. A pacing pulse is delivered 161 to an atrium during a cardiac cycle. If intrinsic activation of the ventricle is not sensed 162 during the cardiac cycle, then a pacing pulse is delivered 163 to the ventricle. The depolarization wavefront initiated by the intrinsic ventricular activation or the ventricular pacing pulse may cause retrograde conduction to the atrium if the atrial pacing pulse did not capture the atrium. The system determines if 164 the atrial pacing pulse captured the atrium. If the system determines that the pacing pulse did not capture the atrium, then atrial retrograde management is provided 165.

In one implementation, the system may detect non-capture if an atrial evoked response is not detected. In this implementation, providing atrial retrograde management may involve delivering an atrial backup pace delivered shortly after the primary atrial pacing pulse.

In another implementation, the system may determine that the atrial pacing pulse did not capture the atrium based on a detected retrograde P-wave. In this implementation, providing retrograde management may involve delaying a next scheduled atrial pacing pulse until after expiration of an atrial effective refractory period as described in more detail below.

Figure 1E:
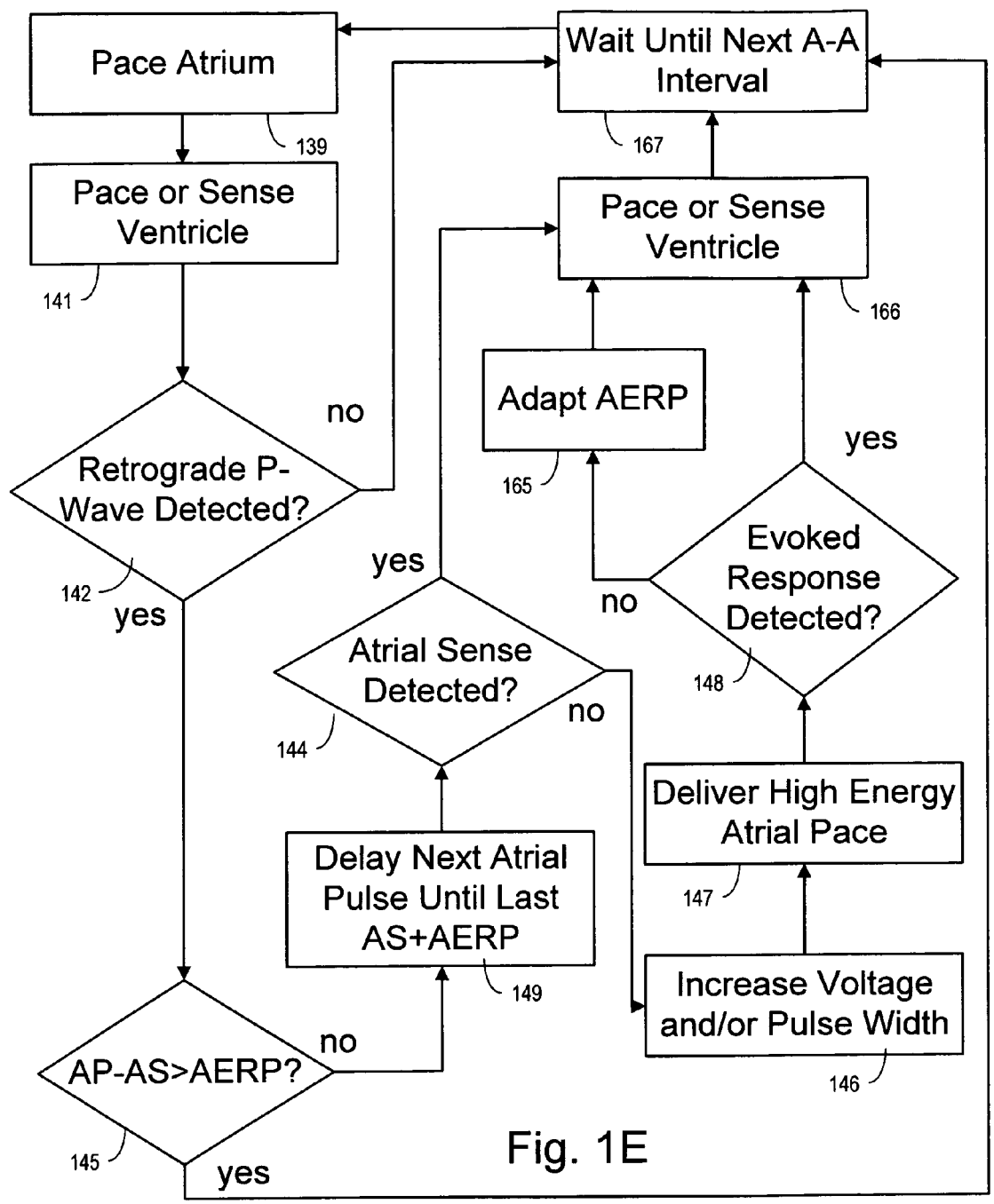
FIG. 1E is a flowchart illustrating in more detail a retrograde conduction management method in accordance with embodiments of the invention.

FIG. 1E is a flowchart illustrating in more detail a retrograde conduction management method in accordance with embodiments of the invention. In this example, the system sensed for a retrograde P-wave and determines that an atrial pacing pulse did not produce capture of the atrium if the retrograde P-wave is sensed. The retrograde P-wave may cause the next scheduled atrial pace to be delivered while the atrial tissue is refractory. The scheduled atrial pace will be ineffective because the atrial tissue will not be able to react to the scheduled atrial pace. The system avoids delivery of atrial pacing while the atrial tissue is refractory, the system delays delivery of the next scheduled atrial pace until after expiration of an atrial effective refractory period (AERP).

In the flowchart of FIG. 1E the system delivers 139 a next scheduled atrial pacing pulse and delivers a ventricular pace if an intrinsic ventricular depolarization is not sensed 141 during an AV interval. Following delivery of the ventricular pace or intrinsic ventricular depolarization, for example, during PVARP, the system senses for 142 a retrograde P-wave. If a retrograde P-wave is not detected 142, then retrograde management is not necessary for the next cycle and the system delivers 139 the next scheduled atrial pulse after an A-A interval has expired 167.

If the retrograde P-wave is detected 142, a check is performed to determine if the time between the retrograde P-wave and the next scheduled atrial pace is longer than an atrial effective refractory period (AERP). For example, a suitable AERP may vary from patient to patient and may be about 200 to 300 milliseconds. If the time is shorter than the AERP, the next atrial pacing pulse is rescheduled 149 by delaying it to occur after the AERP has expired. If the check 145 finds that the time is longer than the AERP, then the timing of the next atrial pacing pulse is not changed, and the system delivers the next atrial pacing pulse as scheduled.

If the next atrial pacing pulse is delayed 149, and there is no atrial sense 144 before that time, then the energy of the delayed atrial pacing pulse may be increased 146 over a previously delivered pacing pulse to ensure capture. A check 148 is then performed to see if an atrial evoked response is detected after delivery of the high energy atrial pacing pulse 147. This step determines if the current AERP is long enough. If the evoked response 148 to the high energy pace 147 is detected, then the AERP is sufficiently long, and the current AERP may be maintained. If there is no evoked response 148 to the high energy atrial pace, then the AERP is insufficient in length and is adjusted 165. If there is no evoked response 148 to the high energy atrial pace, then the AERP is insufficient in length and is adjusted 165. The system paces or senses the ventricle 166 and waits 167 for the next A-A interval.

Figure 1F:
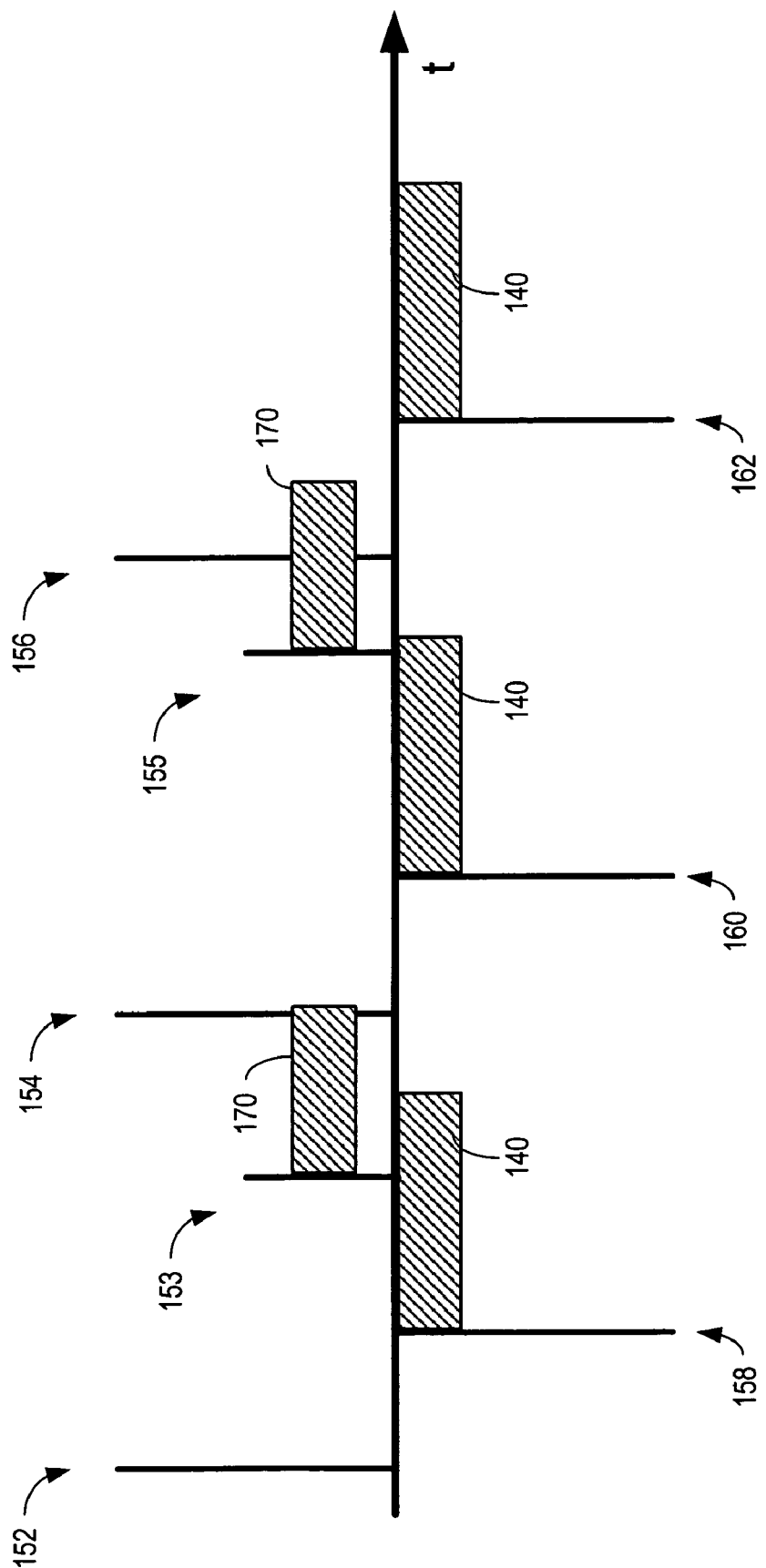
FIGS. 1F and 1G illustrate the operation of a retrograde management method in accordance with embodiments of the invention.
Figure 1G:
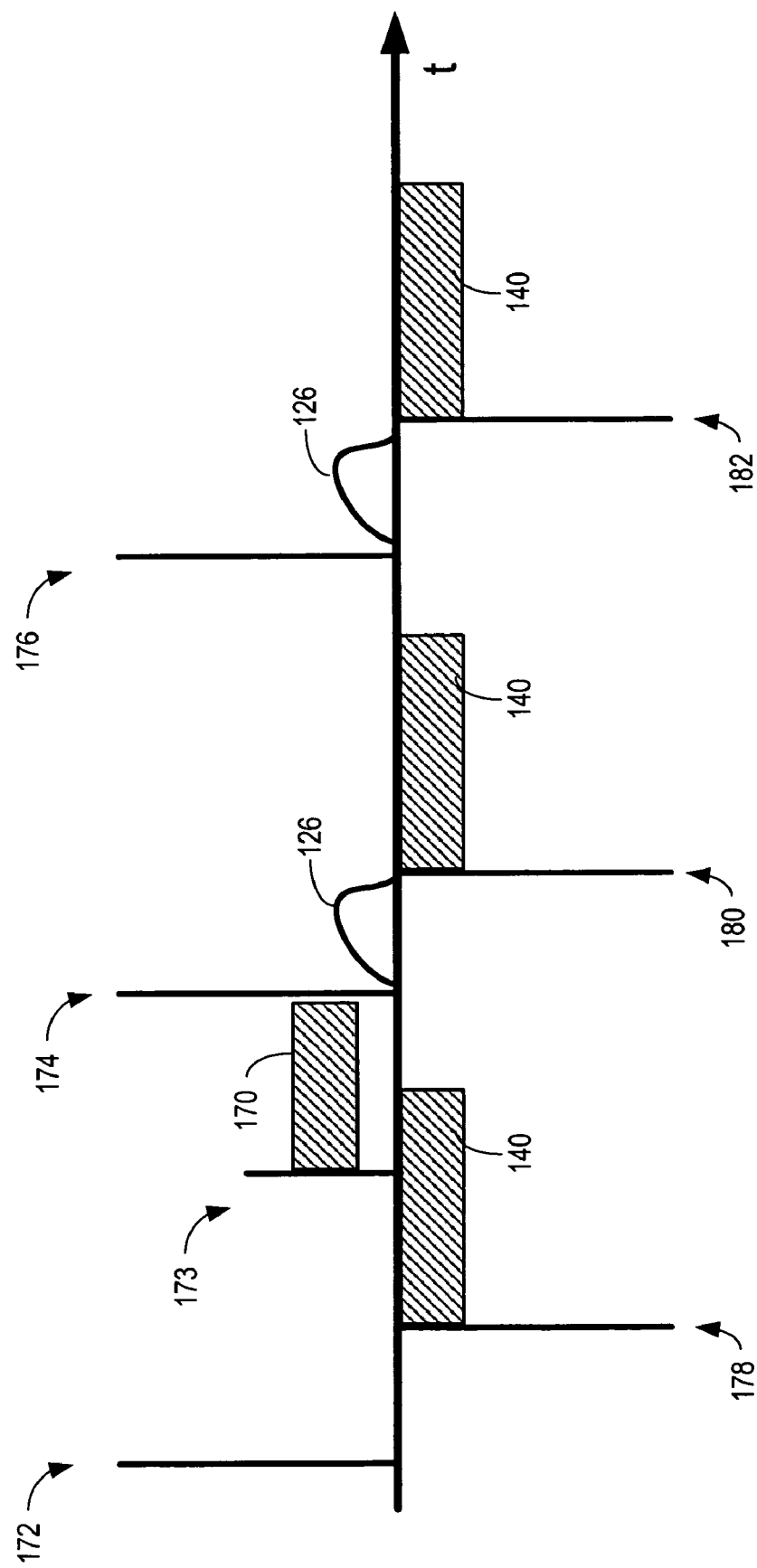

The operation of the retrograde management method described in connection with the flowchart of FIG. 1E is illustrated in the graphs of FIGS. 1F and 1G. FIG. 1F illustrates a pacing response graph of a pacemaker without backup pacing and no retrograde management. In the graph of FIG. 1F, an atrial pace 152 is provided, but capture does not occur. A ventricular pace pulse 158 is delivered after an atrioventricular (AV) delay. The ventricular pace pulse 158 is followed by the PVARP 140. Retrograde conduction occurs, resulting in a retrograde P-wave 153 sensed during the PVARP 140. The PVARP prevents the retrograde P-wave from initiating an AV interval. However, with no retrograde management as discussed above, the next scheduled atrial pace 154 is delivered during the atrial refractory period 170. The atrial pacing pulse 154 is ineffective, setting up another ventricular pace pulse 160 followed by the PVARP 140, and again a retrograde P-wave 155. This process may continue through an ineffective atrial pacing pulse 156 and a subsequent ventricular pacing pulse 162, resulting in repeated ineffective atrial paces and loss of AV synchrony.

FIG. 1G illustrates a pacing response graph of a pacemaker with no backup pacing but having a method of retrograde management in accordance with embodiments of the invention. In the graph of FIG. 1C, an atrial pulse 172 is provided, but capture does not occur. A ventricular pace pulse 178 is provided after an atrioventricular delay. The ventricular pace pulse 178 is followed by the PVARP 140. Retrograde conduction occurs, resulting in retrograde P-wave 173 sensed during the PVARP 140. The pacemaker initiates an AERP 170 relative to the sensed retrograde P-wave 173. Due to the sensed retrograde P-wave 173, the pacemaker delays an atrial pace 174 for the next cardiac cycle until expiration of the AERP 170. Delaying the next scheduled atrial pace 174 until after expiration of the AERP 170 prevents the next scheduled atrial pace 174 from being delivered while the atrial tissue is refractory due to the retrograde P-wave 173. An evoked response signal 126 may be sensed after the atrial pace. AV synchrony and effective atrial pacing are maintained for atrial 176 and ventricular 180, 182 pacing pulses during subsequent cardiac cycles.

The capture verification and retrograde management processes described herein may be utilized in connection with pacing the left and/or right atria. Various embodiments of the invention involve using the same electrode combination for pacing and sensing. Other embodiments involve using an electrode combination for pacing that is different from the electrode combination used to sense the cardiac signal following pacing for capture verification. Employing different electrode combinations for pacing and sensing may enhance cardiac response determination. Further, the same or different electrode combinations may be utilized in sensing for an evoked response and in sensing for a retrograde P-wave.

The embodiments of the present system illustrated herein are generally described as being implemented in an implantable cardiac pacemaker/defibrillator (PD) that may operate in numerous pacing modes known in the art. Various types of single and multiple chamber implantable cardiac defibrillators are known in the art and may be used in connection with the atrial capture verification methods of the present invention. The methods of the present invention may also be implemented in a variety of implantable or patient-external cardiac rhythm management devices, including dual chamber pacemakers, defibrillators, cardioverters, bi-ventricular pacemakers, cardiac resynchronizers, for example.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

Figure 2:
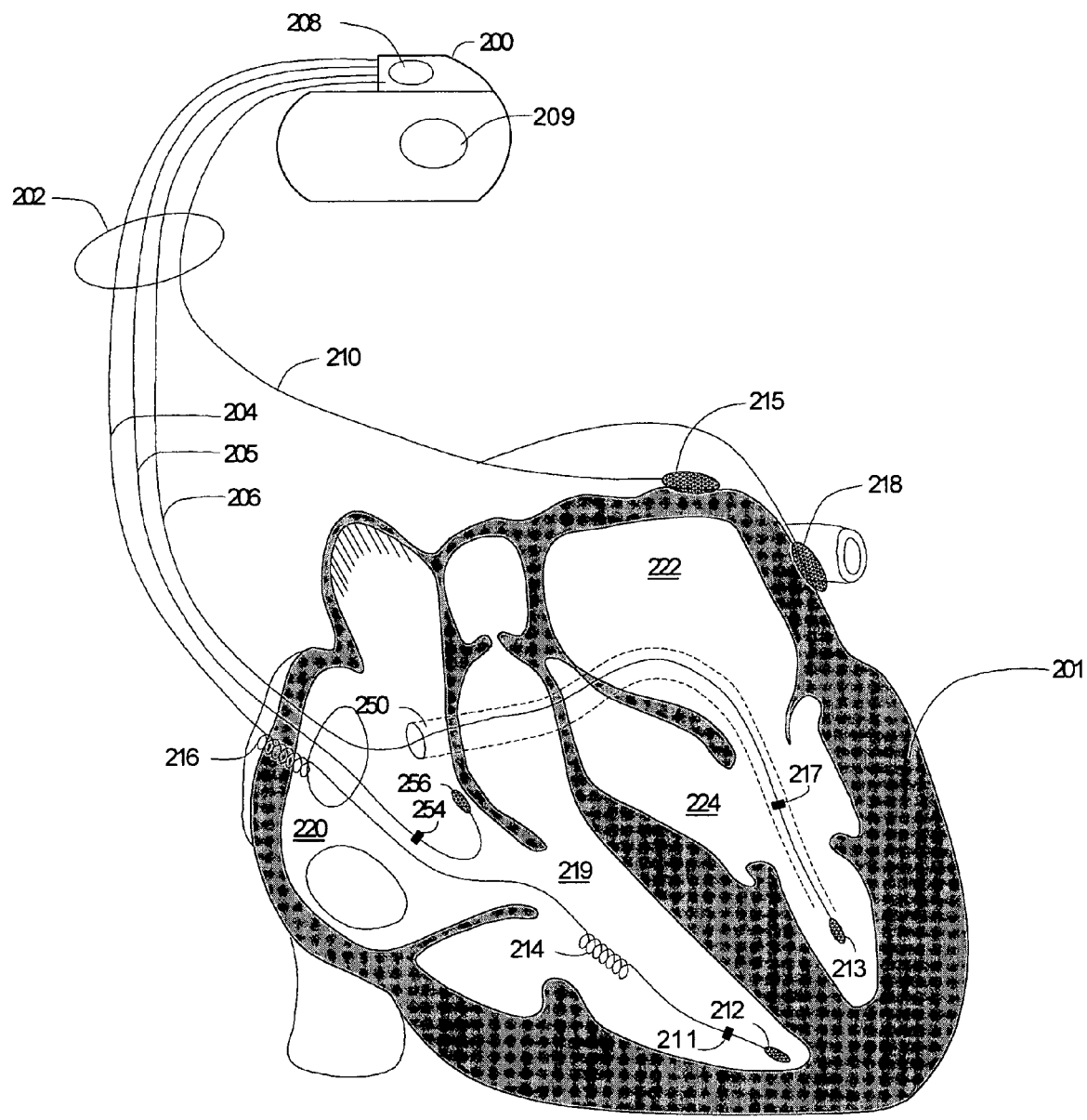
FIG. 2 illustrates an implantable cardiac rhythm management system that may be used in connection with atrial capture verification methodologies in accordance with embodiments of the invention.

Referring now to FIG. 2 of the drawings, there is shown a cardiac rhythm management system that may be used to implement capture verification and retrograde management methods of the present invention. The cardiac rhythm management (CRM) system in FIG. 2 includes a PD 200 electrically and physically coupled to a lead system 202. The housing and/or header of the PD 200 may incorporate one or more electrodes 208, 209 used to provide electrical stimulation energy to the heart and to sense cardiac electrical activity. The PD 200 may utilize all or a portion of the PD housing as a can electrode 209. The PD 200 may include an indifferent electrode 208 positioned, for example, on the header or the housing of the PD 200. If the PD 200 includes both a can electrode 209 and an indifferent electrode 208, the electrodes 208, 209 typically are electrically isolated from each other.

The lead system 202 is used to detect electric cardiac signals produced by the heart 201 and to provide electrical energy to the heart 201 under certain predetermined conditions to treat cardiac arrhythmias. The lead system 202 may include one or more electrodes used for pacing, sensing, and/or defibrillation. In the embodiment shown in FIG. 2, the lead system 202 includes an intracardiac right ventricular (RV) lead system 204, an intracardiac right atrial (RA) lead system 205, an intracardiac left ventricular (LV) lead system 206, and an extracardiac left atrial (LA) lead system 210. The lead system 202 of FIG. 2 illustrates one embodiment that may be used in connection with the methodologies described herein. Other leads and/or electrodes may additionally or alternatively be used.

The lead system 202 may include intracardiac leads 204, 205, 206 implanted in a human body with portions of the intracardiac leads 204, 205, 206 inserted into a heart 290. The intracardiac leads 204, 205, 206 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 2, the lead system 202 may include one or more extracardiac leads 210 having electrodes, e.g., epicardial electrodes, positioned at locations outside the heart for sensing and/or pacing one or more heart chambers.

The right ventricular lead system 204 illustrated in FIG. 2 includes an SVC-coil 216, an RV-coil 214, an RV-ring electrode 211, and an RV-tip electrode 212. The right ventricular lead system 204 extends through the right atrium 220 and into the right ventricle 219. In particular, the RV-tip electrode 212, RV-ring electrode 211, and RV-coil electrode 214 are positioned at appropriate locations within the right ventricle for sensing and delivering electrical stimulation pulses to the heart. The SVC-coil 216 is positioned at an appropriate location within the right atrium chamber of the heart 290 or a major vein leading to the right atrial chamber of the heart 290.

In one configuration, the RV-tip electrode 212 referenced to the can electrode 209 may be used to implement unipolar pacing and/or sensing in the right ventricle. Bipolar pacing and/or sensing in the right ventricle may be implemented using the RV-tip 212 and RV-ring 211 electrodes. In yet another configuration, the RV-ring 211 electrode may optionally be omitted, and bipolar pacing and/or sensing may be accomplished using the RV-tip electrode 212 and the RV-coil 214, for example. The right ventricular lead system 204 may be configured as an integrated bipolar pace/shock lead. The RV-coil 214 and the SVC-coil 216 are defibrillation electrodes.

The left ventricular lead 206 includes an LV distal electrode 213 and an LV proximal electrode 217 located at appropriate locations in or about the left ventricle for pacing and/or sensing the left ventricle. The left ventricular lead 206 may be guided into the right atrium of the heart via the superior vena cava. From the right atrium, the left ventricular lead 206 may be deployed into the coronary sinus ostium, the opening of the coronary sinus. The lead 206 may be guided through the coronary sinus to a coronary vein of the left ventricle. This vein is used as an access pathway for leads to reach the surfaces of the left ventricle that are not directly accessible from the right side of the heart. Lead placement for the left ventricular lead 206 may be achieved via subclavian vein access and a preformed guiding catheter for insertion of the LV electrodes 213, 217 adjacent to the left ventricle.

Unipolar pacing and/or sensing in the left ventricle may be implemented, for example, using the LV distal electrode 213 referenced to the can electrode 209. The LV distal electrode 213 and the LV proximal electrode 217 may be used together as bipolar sense and/or pace electrodes for the left ventricle. The left ventricular lead 206 and the right ventricular lead 204, in conjunction with the PD 200, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 205 includes a RA-tip electrode 256 and an RA-ring electrode 254 positioned at appropriate locations in the right atrium for sensing and pacing the right atrium. In one configuration, the RA-tip 256 referenced to the can electrode 209, for example, may be used to provide unipolar pacing and/or sensing in the right atrium 220. In another configuration, the RA-tip electrode 256 and the RA-ring electrode 254 may be used to effect bipolar pacing and/or sensing.

FIG. 2 illustrates one embodiment of a left atrial lead system 210. In this example, the left atrial lead 210 is implemented as an extracardiac lead with an LA distal electrode 218 and LA proximal electrode 215 positioned at an appropriate locations outside the heart 201 for sensing and pacing the left atrium. Unipolar pacing and/or sensing of the left atrium may be accomplished, for example, using the LA distal electrode 218 to the can 209 pacing vector. Bipolar pacing and/or sensing of the left atrium may be accomplished through the use of the LA distal electrode 218 and the LA proximal electrode 215.

Figure 3:
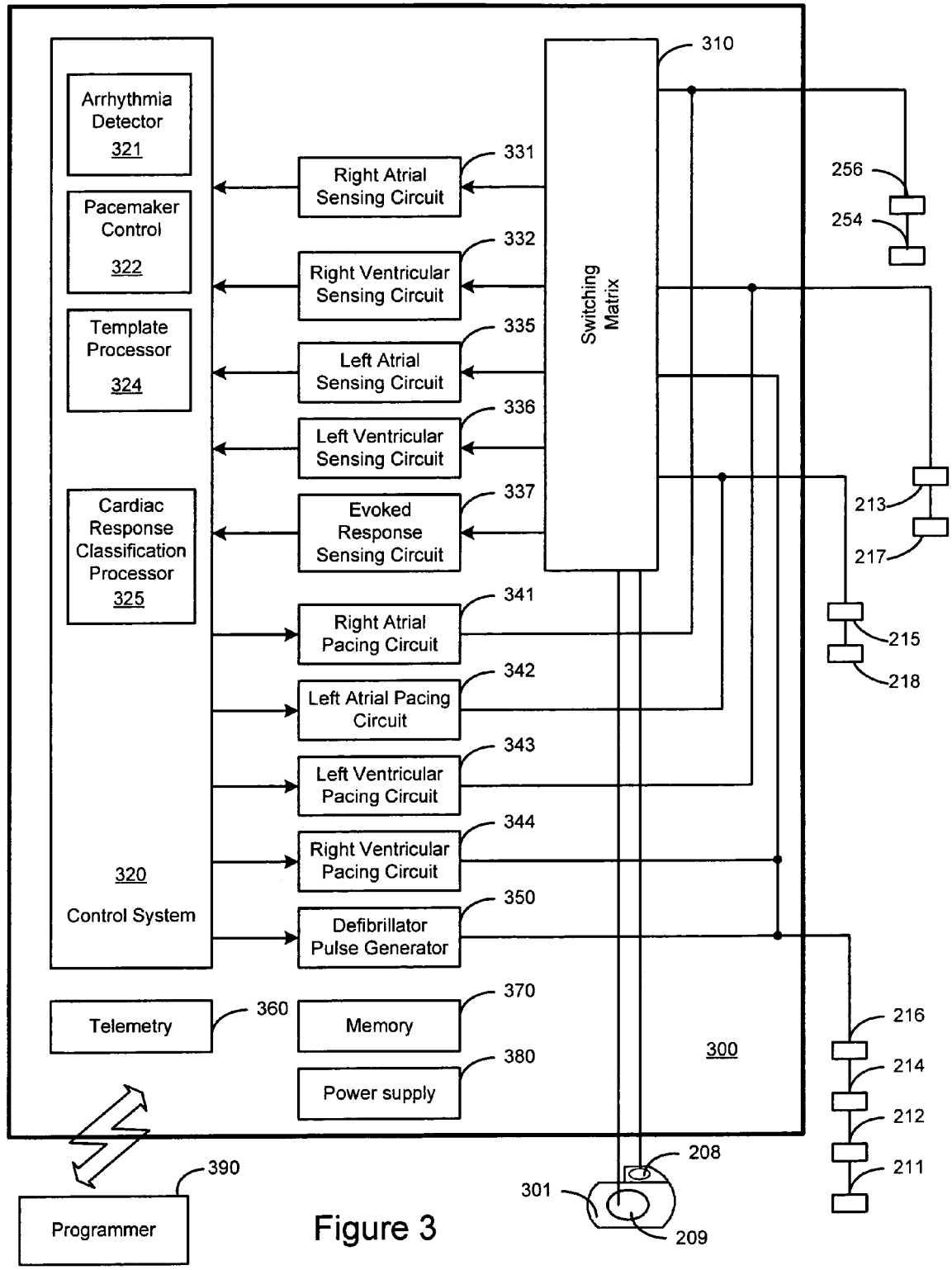
FIG. 3 is a block diagram of an implantable medical device that may be used to verify atrial capture and manage atrial retrograde conduction in accordance with embodiments of the invention.

Referring now to FIG. 3, there is shown an embodiment of a cardiac pacemaker/defibrillator 300 suitable for implementing an atrial capture verification and retrograde management methodologies of the present invention. FIG. 3 shows a cardiac pacemaker/defibrillator divided into functional blocks. It is understood by those skilled in the art that there exist many possible configurations in which these functional blocks can be arranged. The example depicted in FIG. 3 is one possible functional arrangement. Other arrangements are also possible. For example, more, fewer or different functional blocks may be used to describe a cardiac pacemaker/defibrillator suitable for implementing the methodologies of the present invention. In addition, although the cardiac pacemaker/defibrillator 300 depicted in FIG. 3 contemplates the use of a programmable microprocessor-based logic circuit, other circuit implementations may be utilized.

The cardiac pacemaker/defibrillator 300 depicted in FIG. 3 includes circuitry for receiving cardiac signals from a heart and delivering electrical stimulation energy to the heart in the form of pacing pulses or defibrillation shocks. In one embodiment, the circuitry of the cardiac pacemaker/defibrillator 300 is encased and hermetically sealed in a housing 301 suitable for implanting in a human body. Power to the cardiac pacemaker/defibrillator 300 is supplied by an electrochemical battery 380. A connector block (not shown) is attached to the housing 301 of the cardiac pacemaker/defibrillator 300 to allow for the physical and electrical attachment of the lead system conductors to the circuitry of the cardiac pacemaker/defibrillator 300.

The cardiac pacemaker/defibrillator 300 may be a programmable microprocessor-based system, including a control system 320 and a memory 370. The memory 370 may store parameters for various pacing, defibrillation, and sensing modes, along with other parameters. Further, the memory 370 may store data indicative of cardiac signals received by other components of the cardiac pacemaker/defibrillator 300. The memory 370 may be used, for example, for storing historical EGM and therapy data. The historical data storage may include, for example, data obtained from long term patient monitoring used for trending or other diagnostic purposes. Historical data, as well as other information, may be transmitted to an external programmer unit 390 as needed or desired.

The control system 320 may cooperate with other components of the cardiac pacemaker/defibrillator 300 to control the operations of the cardiac pacemaker/defibrillator 300. In one example, the cardiac pacemaker/defibrillator 300 may incorporate a sensor for determining the patient's hemodynamic need. The sensor output may be utilized by the control system 320 to deliver pacing at a rate adapted to the activity level of the patient. In some implementations, the cardiac pacemaker/ defibrillator 300 may include components of an accelerometer and/or a transthoracic impedance sensor for determining the activity level and/or respiration rate of the patient.

The control system 320 depicted in FIG. 3 incorporates a cardiac response classification processor 325 for determining cardiac responses to pacing stimulation in accordance with various embodiments of the present invention. The control system 320 may include additional functional components including a pacemaker control circuit 322, an arrhythmia detector 321, and a template processor 324, along with other components for controlling the operations of the cardiac pacemaker/defibrillator 300.

Telemetry circuitry 360 may be implemented to provide communications between the cardiac pacemaker/defibrillator 300 and an external programmer unit 390. In one embodiment, the telemetry circuitry 360 and the programmer unit 390 communicate using a wire loop antenna and a radio frequency telemetric link, as is known in the art, to receive and transmit signals and data between the programmer unit 390 and the telemetry circuitry 360. In this manner, programming commands and other information may be transferred to the control system 320 of the cardiac pacemaker/defibrillator 300 from the programmer unit 390 during and after implant. In addition, stored cardiac data pertaining to capture threshold, capture detection and/or cardiac response classification, for example, along with other data, may be transferred to the programmer unit 290 from the cardiac pacemaker/defibrillator 300.

In the embodiment of the cardiac pacemaker/defibrillator 300 illustrated in FIG. 3, electrodes RA-tip 256, RA-ring 254, RV-tip 212, RV-ring 211, RV-coil 214, SVC-coil 216, LV distal electrode 213, LV proximal electrode 217, LA distal electrode 218, indifferent electrode 208, and can electrode 209 are coupled through a switch matrix 310 to sensing circuits 331-337.

A right atrial sensing circuit 331 serves to detect and amplify electrical signals from the right atrium of the heart. Unipolar sensing may be implemented, for example, by sensing voltages developed between the RA-tip 256 and the can electrode 209. Outputs from the right atrial sensing circuit are coupled to the control system 320.

A right ventricular sensing circuit 332 serves to detect and amplify electrical signals from the right ventricle of the heart. Right ventricular cardiac signals sensed through use of the RV-tip 212 electrode are right ventricular near-field signals and are denoted RV rate channel signals. A bipolar RV rate channel signal may be sensed as a voltage developed between the RV-tip 212 and the RV-ring 211. Alternatively, bipolar sensing in the right ventricle may be implemented using the RV-tip electrode 212 and the RV-coil 214. Unipolar rate channel sensing in the right ventricle may be implemented, for example, by sensing voltages developed between the RV-tip 212 and the can electrode 209.

Right ventricular cardiac signals sensed through use of defibrillation electrodes are far-field signals, also referred to as RV morphology or RV shock channel signals. More particularly, a right ventricular shock channel signal may be detected as a voltage developed between the RV-coil 214 and the SVC-coil 216. A right ventricular shock channel signal may also be detected as a voltage developed between the RV-coil 214 and the can electrode 209. In another configuration the can electrode 209 and the SVC-coil electrode 216 may be electrically shorted and a RV shock channel signal may be detected as the voltage developed between the RV-coil 214 and the can electrode 209/SVC-coil 216 combination.

Left atrial cardiac signals may be sensed through the use of one or more left atrial electrodes 215, 218, which may be configured as epicardial electrodes. A left atrial sensing circuit 335 serves to detect and amplify electrical signals from the left atrium of the heart. Bipolar sensing and/or pacing in the left atrium may be implemented, for example, using the LA distal electrode 218 and the LA proximal electrode 215. Unipolar sensing and/or pacing of the left atrium may be accomplished, for example, using the vector from the LA distal electrode 218 to can electrode 209 or the LA proximal electrode 215 to can electrode 209.

A left ventricular sensing circuit 336 serves to detect and amplify electrical signals from the left ventricle of the heart. Bipolar sensing in the left ventricle may be implemented, for example, by sensing voltages developed between the LV distal electrode 213 and the LV proximal electrode 217. Unipolar sensing may be implemented, for example, by sensing voltages developed between the LV distal electrode 213 or the LV proximal electrode 217 to the can electrode 209.

Optionally, an LV coil electrode (not shown) may be inserted into the patient's cardiac vasculature, e.g., the coronary sinus, adjacent the left heart. Signals detected using combinations of the LV electrodes, 213, 217, LV coil electrode (not shown), and/or can electrodes 209 may be sensed and amplified by the left ventricular sensing circuitry 336. The output of the left ventricular sensing circuit 236 is coupled to the control system 320.

The outputs of the switching matrix 310 may be operated to couple selected combinations of electrodes 211, 212, 213, 214, 216, 217, 218, 254, and 256 to an evoked response sensing circuit 337. The evoked response sensing circuit 337 serves to sense and amplify voltages developed using various combinations of electrodes for cardiac response classification in accordance with embodiments of the invention.

In the embodiments described below, various combinations of pacing and sensing electrodes may be utilized in connection with pacing and sensing the cardiac signal following the pace pulse to classify the cardiac response to the pacing pulse. For example, in some embodiments, a first electrode combination is used for pacing a heart chamber and a second electrode combination is used to sense the cardiac signal following pacing. In other embodiments, the same electrode combination is used for pacing and sensing. Further, the electrodes used to sense for the retrograde P-wave may be different or the same as the electrodes used to sense for the atrial evoked response.

The pacemaker control circuit 322, in combination with pacing circuitry for the left atrium, right atrium, left ventricle, and right ventricle may be implemented to selectively generate and deliver pacing pulses to the heart using various electrode combinations. The pacing electrode combinations may be used to effect bipolar or unipolar pacing of the heart chambers as described above.

As described above, bipolar or unipolar pacing pulses may be delivered to a heart chamber using one of the pacing vectors as described above. The electrical signal following the delivery of the pacing pulses may be sensed through various sensing vectors coupled through the switch matrix 310 to the cardiac response classification processor 325 and used to classify the cardiac response to pacing.

The switching matrix 310 may be arranged to provide connections to various configurations of pacing and defibrillation electrodes. The outputs of the switching matrix 310 may be coupled to an evoked response (ER) sensing circuit 337 that serves to sense and amplify cardiac signals detected between the selected combinations of electrodes. The detected signals are coupled through the ER amplifier 337 to a cardiac response classification processor 325. The cardiac response classification processor 325 includes circuitry configured to determine the cardiac response to a pacing stimulation. The presence or absence of an evoked response may be determined based on the amplitude, peak value, peak timing, and/or other morphological features of the cardiac signal sensed following the pacing pulse in accordance with embodiments of the invention.

In one implementation, the cardiac pacemaker/defibrillator 300 may utilize the evoked response channel 337 to sense for the atrial evoked response (AER) as described herein. The cardiac pacemaker/defibrillator 300 may utilize the right atrial sensing channel 331 to sense for retrograde P-waves in the right atrium. The cardiac pacemaker/defibrillator 300 may utilize the left atrial sensing channel 335 to sense for retrograde P-waves in the left atrium.

Figure 4A:
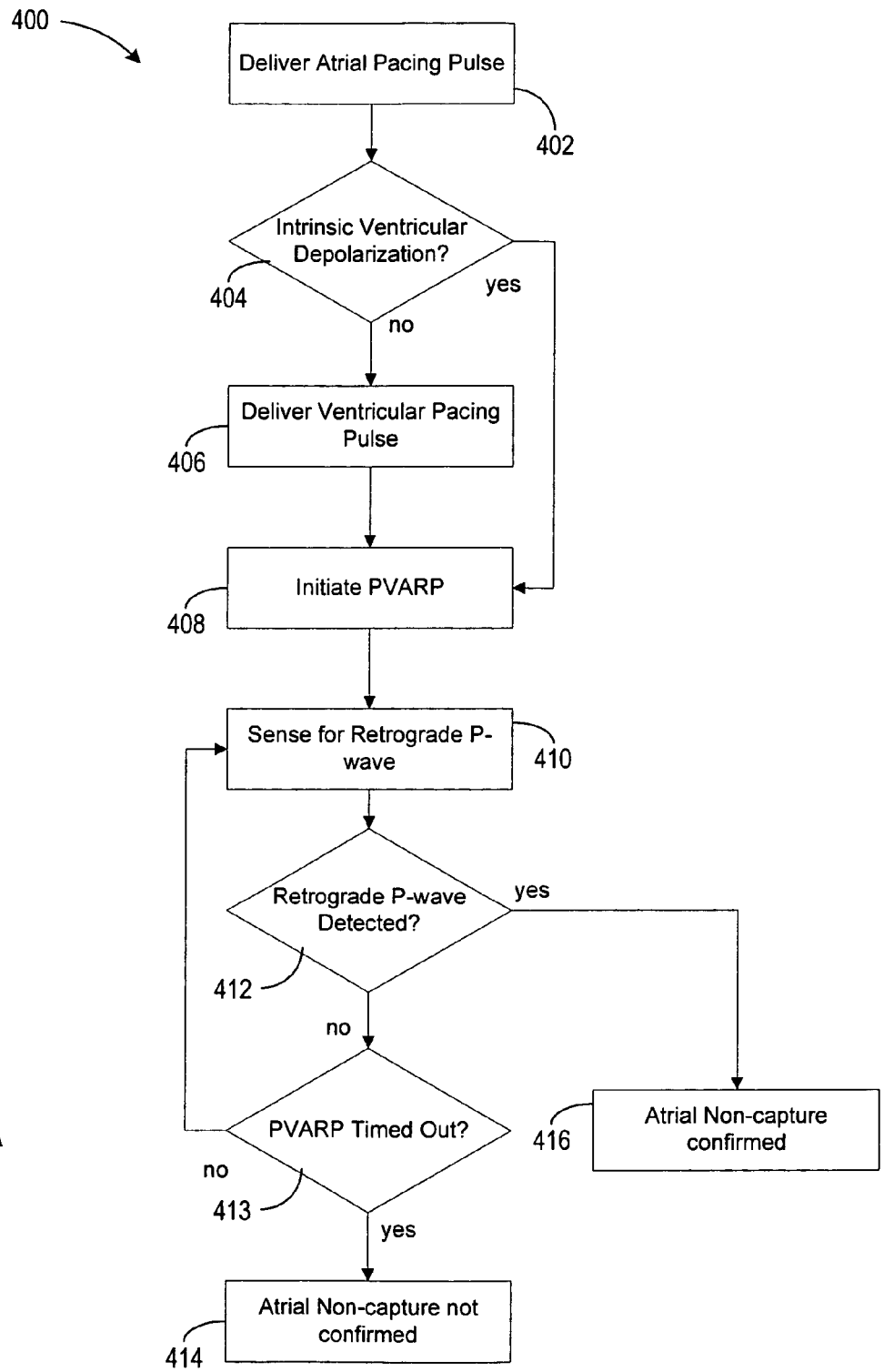
FIG. 4A is a flowchart of a method of capture detection based on retrograde conduction in accordance with the present invention.

FIG. 4A is a flowchart further describing methods 400 of capture detection based on retrograde conduction in accordance with the present invention. An atrial pacing pulse 402 is delivered, and a check 404 is made to detect intrinsic ventricular depolarization. If the check 404 finds no ventricular depolarization, a ventricular pacing pulse 406 is delivered. A PVARP 408 is initiated following the ventricular pacing pulse or the intrinsic ventricular depolarization. After initiating PVARP 408, the system senses 410 for a retrograde P-wave. If the retrograde P-wave is detected 412, during 413 PVARP, then atrial non-capture 416 is confirmed. If the retrograde P-wave is not detected 412 during 413 PVARP, atrial non-capture 414 is not confirmed.

Figure 4B:
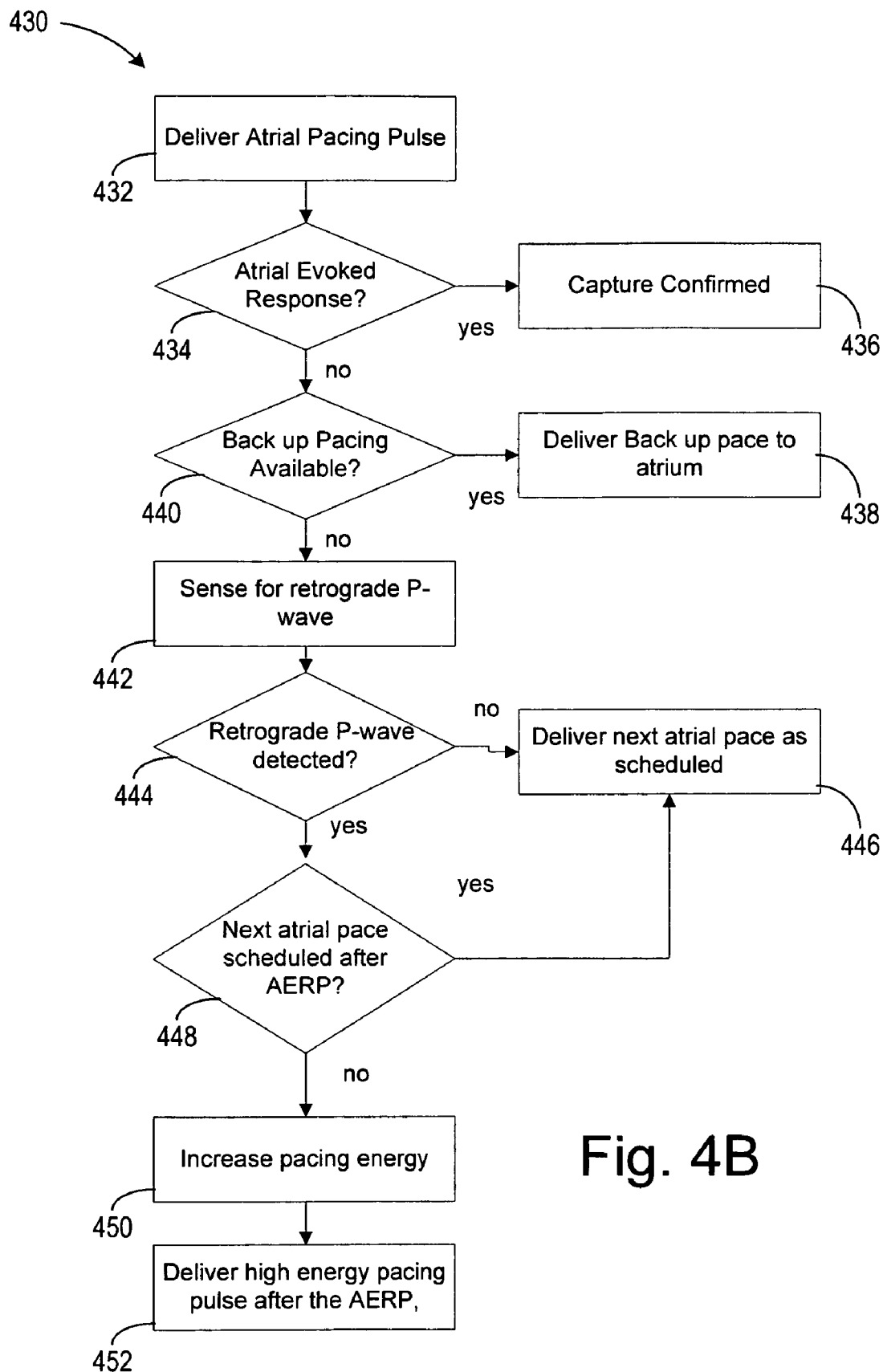
FIG. 4B is a flowchart of a method of retrograde management in accordance with the present invention.

FIG. 4B is a flowchart of a method 430 of retrograde management in accordance with the present invention. Atrial pacing pulse 432 is delivered, and a check 434 is made to detect an atrial evoked response. If the check 434 finds no atrial evoked response, and backup pacing 440 is not available, then a sense 442 is done for a retrograde P-wave. If a retrograde P-wave is detected 444, and the next atrial pulse is scheduled 448 after AERP, the next atrial pulse is delivered 446 as scheduled. If the next atrial pace is not scheduled 448 after AERP, then the pacing energy is increased 450 and a high energy pacing pulse is delivered 452 after the AERP. If, at the check 434 for atrial evoked response, an evoked response is detected, then capture is confirmed 436. If the atrial evoked response is not detected at check 434, but backup pacing 440 is available, then backup pacing is delivered 438 to the atrium. If a retrograde P-wave is not detected 444, the next atrial pace 446 may be delivered as scheduled.

Figure 4C:
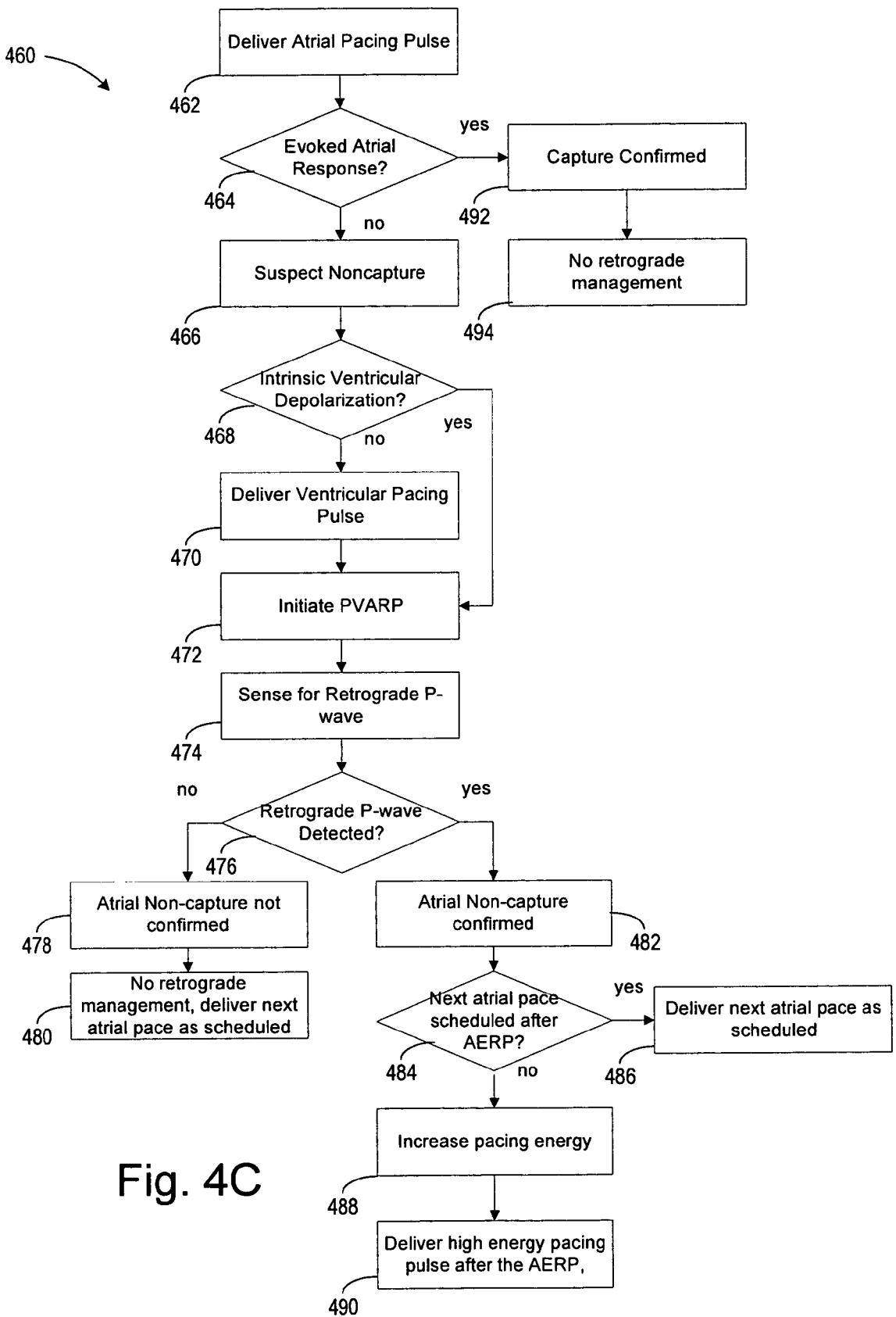
FIG. 4C is a flowchart of a method of capture detection and retrograde management in accordance with the present invention.

FIG. 4C is a flowchart of a method 460 of capture verification and retrograde management in accordance with the present invention. Atrial pacing pulse 462 is delivered, and a check 464 is made to detect an atrial evoked response 464. If there is a detected atrial evoked response 464, then capture is confirmed 492, and no retrograde management 494 is used. If there is no detected atrial evoked response 464, then non-capture is suspected 466, and a check for intrinsic ventricular depolarization 468 is performed. If the check 468 finds no ventricular depolarization, a ventricular pacing pulse 470 is delivered. If the check 468 finds a ventricular depolarization, a PVARP 472 is initiated without the ventricular pacing pulse 470. After initiating PVARP 472, a sense 474 is made for a retrograde P-wave. If the retrograde P-wave is detected 476, atrial non-capture 482 is confirmed, and a check 484 is performed to see if the next atrial pace is scheduled after the AERP. If the check 484 determines that the pace is scheduled after the AERP, then the next atrial pulse is delivered 486 as scheduled. If the check 484 determines that the pace is not scheduled after the AERP, then the pacing energy is increased 488 and the higher energy pulse is delivered 490 after the AERP. If the retrograde P-wave is not detected at 476, atrial non-capture 478 is not confirmed, and no retrograde management 480 is used, so the next atrial pulse is delivered as scheduled.

A number of the examples presented herein involve block diagrams illustrating functional blocks used for coordinated monitoring, diagnosis and/or therapy functions in accordance with embodiments of the present invention. It will be understood by those skilled in the art that there exist many possible configurations in which these functional blocks can be arranged and implemented. The examples depicted herein provide examples of possible functional arrangements used to implement the approaches of the invention.

It is understood that the components and functionality depicted in the figures and described herein can be implemented in hardware, software, or a combination of hardware and software. It is further understood that the components and functionality depicted as separate or discrete blocks/elements in the figures in general can be implemented in combination with other components and functionality, and that the depiction of such components and functionality in individual or integral form is for purposes of clarity of explanation, and not of limitation.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of classifying a cardiac response to pacing, comprising:
  delivering a first pacing pulse to an atrium during a first cardiac cycle;
  sensing for an atrial evoked response following delivery of and associated with the first atrial pacing pulse
  sensing for an intrinsic activation of a ventricle during the first cardiac cycle;
  delivering a pacing pulse to the ventricle if the intrinsic ventricular activation is not sensed during the first cardiac cycle;
  sensing in the atrium for a retrograde P-wave, the retrograde P-wave responsive to the ventricular pacing pulse or the intrinsic ventricular activation;
  classifying the cardiac response to the first atrial pacing pulse as a non-captured response if the retrograde P-wave is detected and the atrial evoked response is not detected; and
  classifying the cardiac response to the first atrial pacing pulse as a captured response if the atrial evoked response is detected and the retrograde P-wave is not detected.

2. The method of claim 1, wherein sensing for the retrograde P-wave comprises sensing for the retrograde P-wave during a time interval following sensing intrinsic ventricular activity or delivery of the ventricular pacing pulse.

3. The method of claim 2, wherein the time interval comprises a post ventricular atrial refractory period.

4. The method of claim 2, wherein the time interval begins about 100 milliseconds following delivery of the ventricular pacing pulse and ends about 500 milliseconds following delivery of the ventricular pacing pulse.

5. The method of claim 1, further comprising:
  delivering additional atrial pacing pulses during cardiac cycles subsequent to the cardiac cycle;
  delivering additional ventricular pacing pulses during the subsequent cardiac cycles;

sensing in the atrium for retrograde P-waves, the retrograde P-waves respectively responsive to the additional ventricular pacing pulses; and classifying cardiac responses to the additional atrial pacing pulses as non-captured responses if the retrograde P-waves are detected.

6. The method of claim 5, wherein delivering atrial pulses, delivering ventricular pulses, sensing in the atrium, and classifying the cardiac responses are performed beat by beat during a pacing therapy delivered to a patient.

7. The method of claim 5, wherein delivering the atrial pacing pulses, delivering the ventricular pacing pulses, sensing in the atrium, and classifying the cardiac responses are performed during a test to determine a capture threshold of the atrium.

8. The method of claim 1, wherein sensing in the atrium for a retrograde P-wave comprises sensing in the atrium during a post ventricular atrial refractory period.

9. The method of claim 1, further comprising:
delivering additional atrial pacing pulses during cardiac cycles subsequent to the cardiac cycle;
sensing for atrial evoked responses following delivery of the additional atrial pacing pulses;
sensing in the atrium for retrograde P-waves, the retrograde P-waves responsive to ventricular pacing pulses or the intrinsic ventricular activations during the subsequent cardiac cycles; and
classifying the cardiac responses to the additional atrial pacing pulses based on the sensed atrial evoked responses and the sensed retrograde P-waves, wherein delivering the atrial pacing pulses, sensing in the atrium, and classifying the cardiac responses are performed beat by beat during a pacing therapy delivered to a patient.

10. The method of claim 1, further comprising:
delivering additional atrial pacing pulses during cardiac cycles subsequent to the cardiac cycle;
sensing for atrial evoked responses following delivery of the additional atrial pacing pulses;
sensing in the atrium for retrograde P-waves, the retrograde P-waves responsive to ventricular pacing pulses or the intrinsic ventricular activations during the subsequent cardiac cycles; and
classifying the cardiac responses to the additional atrial pacing pulses based on the sensed atrial evoked responses and the sensed retrograde P-waves, wherein delivering the atrial pacing pulses, sensing in the atrium, and classifying the cardiac responses are performed during a test to determine a capture threshold of the atrium.

11. The method of claim 1, further comprising:
delivering, during a second cardiac cycle immediately following the first cardiac cycle, a second atrial pacing pulse to the atrium, the second atrial pacing pulse having an increased energy relative to the first atrial pacing pulse if the cardiac response of the first atrial pacing pulse is classified as a non-captured response.

12. The method of claim 1, further comprising:
delivering, during a second cardiac cycle immediately following the first cardiac cycle, a second atrial pacing pulse to the atrium, the second atrial pacing pulse having a scheduled delivery time, but the second atrial pacing pulse being delivered at a time that is delayed relative to the scheduled delivery time if the cardiac response of the first atrial pacing pulse is classified as a non-captured response and if a time period between the detected retrograde P-wave and the scheduled delivery time is no greater than an atrial effective refractory period (AERP).

13. The method of claim 12, further comprising:
increasing the AERP if the second atrial pacing pulse does not capture the atrium.

14. The method of claim 12, wherein the second atrial pacing pulse is delivered at an increased energy relative to the first atrial pacing pulse if the cardiac response of the first atrial pacing pulse is classified as a non-captured response.

15. A cardiac system, comprising:
first means for delivering a first pacing pulse to an atrium during a first cardiac cycle;
means for sensing for an atrial evoked response following delivery of and associated with the first atrial pacing pulse;
means for sensing for an intrinsic activation of a ventricle during the first cardiac cycle;
means for delivering a pacing pulse to the ventricle if the intrinsic ventricular activation is not sensed during the first cardiac cycle;
means for sensing in the atrium for a retrograde P-wave, the retrograde P-wave responsive to the ventricular pacing pulse or the intrinsic ventricular activation;
means for classifying the cardiac response to the first atrial pacing pulse as a non-captured response if the retrograde P-wave is detected and the atrial evoked response is not detected, and for classifying the cardiac response to the first atrial pacing pulse as a captured response if the atrial evoked response is detected and the retrograde P-wave is not detected.

16. The cardiac system of claim 15, further comprising means for delivering the pacing pulse is configured to deliver, during a second cardiac cycle immediately following the first cardiac cycle, a second atrial pacing pulse to the atrium, the second atrial pacing pulse having an increased energy relative to the first atrial pacing pulse if the classifying means classifies the cardiac response of the first atrial pacing pulse as a non-captured response.

17. The cardiac system of claim 15, further comprising:
second means for delivering, during a second cardiac cycle immediately following the first cardiac cycle, a second atrial pacing pulse to the atrium, the second atrial pacing pulse having a scheduled delivery time, but the second delivering means being configured to deliver the second atrial pacing pulse at a time that is delayed relative to the scheduled delivery time if the classifying means classifies the cardiac response of the first atrial pacing pulse as a non-captured response and if a time period between the detected retrograde P-wave and the scheduled delivery time is no greater than an atrial effective refractory period (AERP).

18. The cardiac system of claim 17, further comprising:
means for increasing the AERP if the second atrial pacing pulse does not capture the atrium.

19. The cardiac system of claim 17, wherein the second delivering means delivers the second atrial pacing pulse at an increased energy relative to the first atrial pacing pulse if the classifying means classifies the cardiac response of the first atrial pacing pulse as a non-captured response.

* * * * *

UNITED STATES PATENT AND TRADEMARK OFFICE
CERTIFICATE OF CORRECTION

PATENT NO. : 7,587,240 B2  Page 1 of 1
APPLICATION NO. : 11/012433
DATED : September 8, 2009
INVENTOR(S) : Zhang et al.

It is certified that error appears in the above-identified patent and that said Letters Patent is hereby corrected as shown below:

Title Page item 57
In the Abstract:

Line 4 of Abstract: "patient'heart" should read --patient's heart--.

Signed and Sealed this

Fifth Day of January, 2010

David J. Kappos
*Director of the United States Patent and Trademark Office*

UNITED STATES PATENT AND TRADEMARK OFFICE
CERTIFICATE OF CORRECTION

PATENT NO.       : 7,587,240 B2
APPLICATION NO.  : 11/012433
DATED            : September 8, 2009
INVENTOR(S)      : Zhang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 512 days.

Signed and Sealed this

Fourteenth Day of December, 2010

David J. Kappos
*Director of the United States Patent and Trademark Office*